United States Patent
Hirschel et al.

(10) Patent No.: US 8,734,403 B2
(45) Date of Patent: May 27, 2014

(54) BLOCKING ELEMENT FOR A DOSING MECHANISM

(75) Inventors: Juerg Hirschel, Aarau (CH); Ulrich Moser, Heimiswil (CH); Christian Schrul, Burgdorf (CH); Markus Tschirren, Kirchberg (CH)

(73) Assignee: TecPharma Licensing AG, Burgdorf (CH)

( * ) Notice: Subject to any disclaimer, the term of this patent is extended or adjusted under 35 U.S.C. 154(b) by 556 days.

(21) Appl. No.: 12/371,324

(22) Filed: Feb. 13, 2009

(65) Prior Publication Data

US 2009/0227959 A1 Sep. 10, 2009

Related U.S. Application Data

(63) Continuation of application No. PCT/CH2007/000397, filed on Aug. 14, 2007.

(30) Foreign Application Priority Data

| Aug. 14, 2006 | (DE) | .......................... 10 2006 038 123 |
| Aug. 14, 2006 | (DE) | ..................... 20 2006 019 890 U |
| Dec. 6, 2006 | (DE) | .......................... 10 2006 057 578 |
| Dec. 22, 2006 | (DE) | ..................... 20 2006 019 370 U |
| Jan. 9, 2007 | (DE) | .......................... 10 2007 001 432 |

(51) Int. Cl.
*A61M 5/00* (2006.01)
(52) U.S. Cl.
USPC .......................... 604/210; 604/207; 604/187
(58) Field of Classification Search
USPC .................. 604/207–211, 181, 187
See application file for complete search history.

(56) References Cited

U.S. PATENT DOCUMENTS

| 3,353,718 | A | 11/1967 | McLay |
| 5,092,842 | A | 3/1992 | Bechtold et al. |
| 5,112,317 | A | 5/1992 | Michel |
| 5,378,233 | A | 1/1995 | Haber et al. |
| 5,383,865 | A | 1/1995 | Michel |
| 5,647,856 | A | 7/1997 | Eykmann et al. |
| 6,004,298 | A | 12/1999 | Levander |
| 6,048,336 | A | 4/2000 | Gabriel |
| 6,793,646 | B1 * | 9/2004 | Giambattista et al. .......... 604/90 |

(Continued)

FOREIGN PATENT DOCUMENTS

| DE | 0 635 934 | 10/1936 |
| DE | 198 21 934 C1 | 11/1999 |

(Continued)

*Primary Examiner* — Bhisma Mehta
*Assistant Examiner* — Bradley G Thomas, Jr.
(74) *Attorney, Agent, or Firm* — Dorsey & Whitney LLP; Stuart R. Hemphill, Esq.

(57) ABSTRACT

A lock for a dosing mechanism of an injection device, the lock including at least one holding element that interacts with the dosing mechanism, or with a dosing element of the dosing mechanism, whereby an adjustment movement of the dosing mechanism or the dosing element is prevented in a starting position of the lock and is possible only after a movement or displacement of the lock or the holding element. An injection device used in conjunction with a two-chamber ampoule is encompassed, as is a method for preparing the injection device for dispensing a substance wherein the ampoule is introduced into the injection device and a lock is released when the ampoule has been introduced far enough to appropriately mix the substances in the two chambers, whereupon the mixed substances can be dispensed from the ampoule.

17 Claims, 2 Drawing Sheets

(56) References Cited

U.S. PATENT DOCUMENTS

| | | | |
|---|---|---|---|
| 2004/0186431 A1 | 9/2004 | Graf et al. | |
| 2004/0186443 A1 | 9/2004 | Covino et al. | |
| 2005/0065477 A1 * | 3/2005 | Jost | 604/207 |
| 2005/0137571 A1 * | 6/2005 | Hommann | 604/500 |
| 2005/0154351 A1 | 7/2005 | Graf et al. | |
| 2005/0222540 A1 | 10/2005 | Kirchhofer | |
| 2005/0261634 A1 | 11/2005 | Karlsson | |

FOREIGN PATENT DOCUMENTS

| | | |
|---|---|---|
| DE | 697 21 700 | 3/2004 |
| DE | 699 22 027 | 10/2005 |
| DE | 10 2004 055 298 | 5/2006 |
| DE | 603 02 335 | 8/2006 |
| EP | 0 554995 A | 8/1993 |
| EP | 0 937 471 | 8/1999 |
| WO | WO 00/41752 | 7/2000 |
| WO | WO 00/62839 A | 10/2000 |
| WO | WO 01/72361 | 10/2001 |
| WO | WO 02/092153 A | 11/2002 |
| WO | WO 03/000317 | 1/2003 |
| WO | WO 03/053499 | 7/2003 |
| WO | WO 2004/006997 | 1/2004 |
| WO | WO 2005/072796 | 8/2005 |
| WO | WO 2007/082400 | 7/2007 |

* cited by examiner

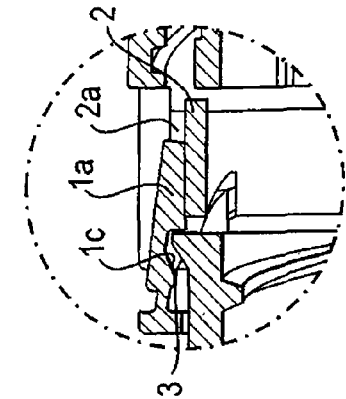
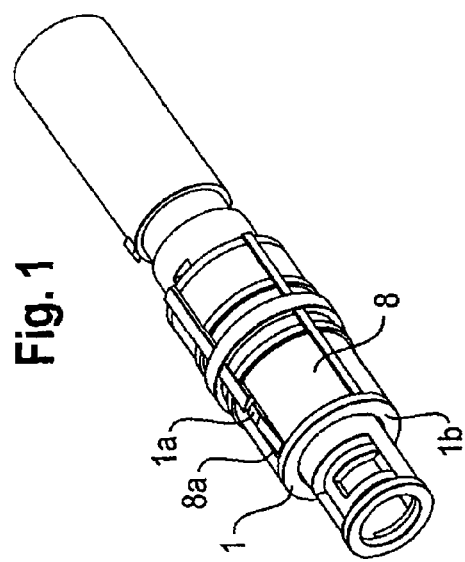
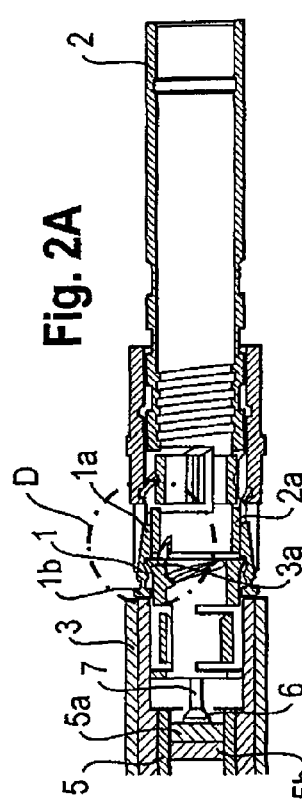
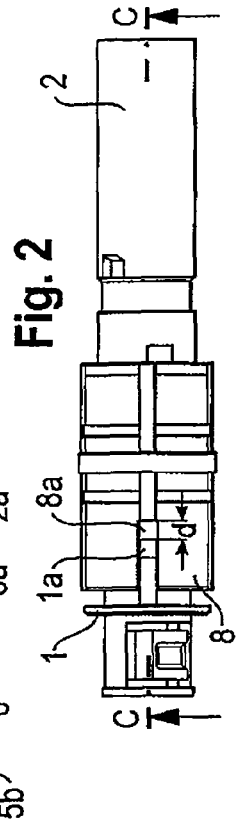
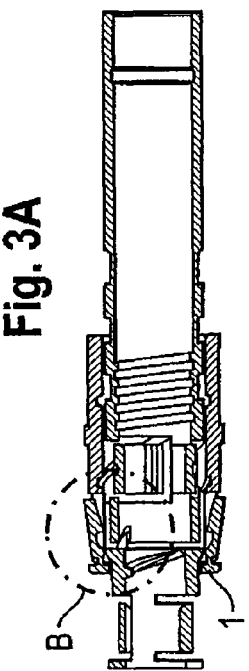
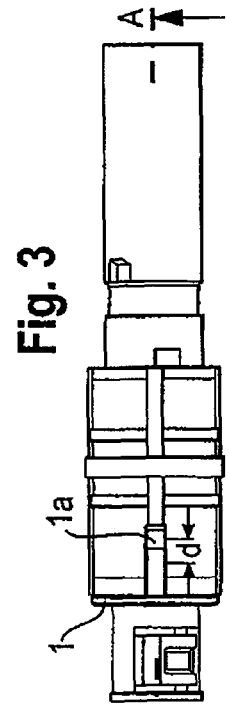

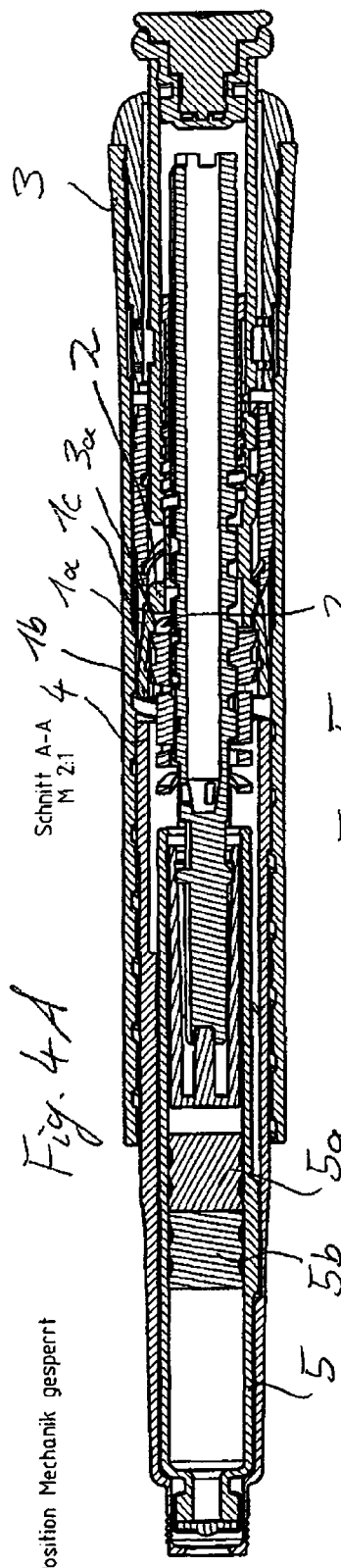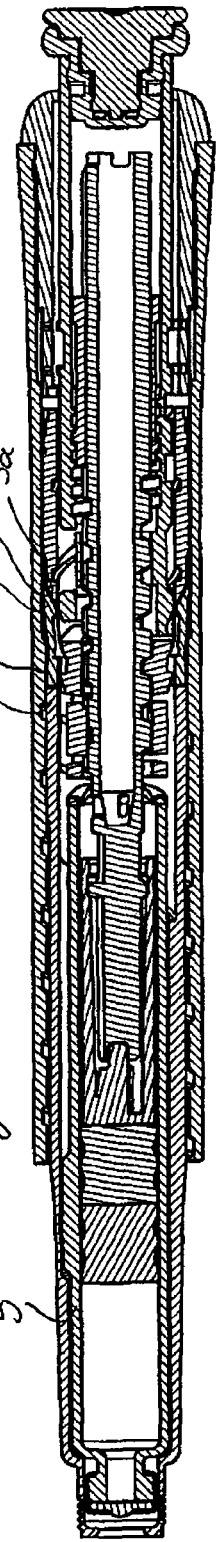

BLOCKING ELEMENT FOR A DOSING MECHANISM

CROSS-REFERENCED RELATED APPLICATIONS

This application is a continuation of International Patent Application No. PCT/CH2007/000397 filed Aug. 14, 2007, which claims priority to German Patent Application No. DE 10 2006 038 123.8 filed Aug. 14, 2006, German Patent Application No. DE 20 2006 019 890.3 filed Aug. 14, 2006, German Patent Application No. DE 10 2006 057 578.4 filed Dec. 6, 2006, German Patent Application No. DE 20 2006 019 370.7 filed Dec. 22, 2006 and German Patent Application No. DE 10 2007 001 432.7 filed Jan. 9, 2007, the entire content of all of which is incorporated herein by reference.

BACKGROUND

The present invention relates to devices for delivering, injecting, infusing, dispensing or administering a substance, and to methods of making and using such devices. More particularly, it relates to devices, structures and/or mechanisms for setting, controlling or selecting an amount or dose of a substance to be injected or dispensed from such devices. More particularly, it relates to a lock element for locking a dose setting mechanism of an injection device, e.g. an injection device for use with a two-chamber ampoule in which two substances are contained separately from one another and are mixed prior to administering by the injection device.

If a two-chamber ampoule is incompletely or only partially screwed into an injection device, there is a possibility that the substances contained in the two-chamber ampoule will not be mixed or will be only partially mixed, in which case unmixed substances or an incompletely mixed substance could be dispensed during an injection operation.

SUMMARY

One object of the present invention is to provide an element for injection devices, by which the use of injection devices can be made more reliable, including in conjunction with two-chamber ampoules.

In one embodiment, a lock element in accordance with the present invention is used to lock a setting, priming or dose setting mechanism or a setting, priming or dose setting element of an injection device, e.g. a disposable injector or an injection pen.

In one embodiment, the present invention comprises a lock for a dosing mechanism of an injection device, the lock including at least one holding element that interacts with the dosing mechanism, or with a dosing element of the dosing mechanism, whereby an adjustment movement of the dosing mechanism or the dosing element is prevented in a starting position of the lock and is possible only after a movement or displacement of the lock or the holding element. An injection device used in conjunction with a two-chamber ampoule is encompassed, as is a method for preparing the injection device for dispensing a substance wherein the ampoule is introduced into the injection device and a lock is released when the ampoule has been introduced far enough to appropriately mix the substances in the two chambers, whereupon the mixed substances can be dispensed from the ampoule.

In one embodiment, the invention comprises a blocking element for a dosing mechanism of an injection device with at least one holding element that can interact with the dosing mechanism, or with a dosing element of the dosing mechanism, in such a way that an adjustment movement of the dosing mechanism or of the dosing element can be prevented in a starting position of the blocking element and is permitted only after a movement or displacement of the blocking element or of the holding element. The invention also relates to a method for preparing an injection device for dispensing a substance from an ampoule or two-chamber ampoule, wherein the ampoule or two-chamber ampoule is introduced, e.g. screwed, into the injection device, and the blocking or anti-rotational locking of the dosing or adjusting element or a lifting element of the injection device is only released when the ampoule has been introduced so far into the injection device that a substance can be dispensed from the ampoule in a defined or dosed manner, and/or that the substances contained in the two-chamber ampoule are appropriately or properly, e.g. completely, mixed.

In one embodiment, the lock element has at least one displaceable, e.g. flexible, retaining element, which is able to co-operate with the dose setting mechanism or dose setting element of the injection device so that a priming, dose setting, or setting movement or operation can be prevented and/or precluded. In some embodiments, the movement or operation, such as a rotating or sliding movement or an extraction movement of the dose setting element is prevented when the lock element is in an initial position due to a catch connection to the lock element, and is not triggered or initiated until the at least one retaining element has been displaced or moved, for example by a sliding movement of the lock element caused by or after introducing an ampoule.

In some embodiments, a lock element in accordance with the present invention prevents a dose setting mechanism and/or a setting or dose setting element from being operated to set a dose or prime an injection device before an ampoule is loaded in the injection device. In some embodiments, the ampoule may be a two-chamber ampoule which makes contact with the lock element, and it and/or the lock element has been pushed into or moved relative to the injection device by a pre-defined distance, e.g. 2 mm, thereby releasing the dose setting mechanism, for example by moving a retaining element engaging the dose setting mechanism.

In some embodiments, the lock element is in the form of a ring and has a contact surface for contacting an ampoule or ampoule sleeve, so that an ampoule fully or almost fully inserted or screwed into the injection device moves into contact with the lock element and drives or moves it relative to the injection device or relative to the setting mechanism on the last part of the distance of the pushing-in or screwing-in movement. In some embodiments, the at least one retaining element is biased radially inwardly or radially outwardly, and locates or is receiveable in a recess or groove of a dose setting element or a dose setting device to prevent a rotating movement or extraction of the dose setting element, e.g. the lock element is fitted in or with the injection device to afford an anti-rotation lock. In some embodiments, two or more retaining elements are provided, for example two retaining elements opposite one another on an annular lock element, which can be biased radially inwardly and locate in, lodge in or be connected to the dose setting mechanism or a dose setting element in an initial position when the ampoule has not yet been fully inserted, and/or are not pushed radially outwardly to release the dose setting element or dose setting mechanism until an ampoule has been introduced.

Another aspect of the present invention relates to a dose setting mechanism for an injection device, wherein the does setting mechanism has a lock element of the type described above and at least one dose setting element, e.g. a rotating knob or a rotating sleeve. In some preferred embodiments, the dose setting element has at least one retaining or locating element or a recess, such as a groove, with which the at least one retaining element of the lock element co-operates, i.e. in which it locates. The lock element is mounted so that it is able to slide, e.g. axially, relative to the dose setting element toward, through or out of it. The at least one retaining element of the lock element may be such that during or after a sliding movement of the lock element relative to the dose setting element, the retaining element or elements is or are moved or pushed by a ramp or inclined surface that does not slide with the lock element so that a coupling no longer exists between the lock element and the dose setting mechanism or dose setting element, which means that the dose setting element or dose setting mechanism can be operated and rotated or pulled out of the injection device to set a dose or prime the injection device.

The expression "retaining element" as used herein is intended to encompass and/or mean any element, feature, structure or the like, e.g. a recess or bore, that enables a coupling or connection, e.g., an anti-rotation lock, with another element. For example, a displaceable or flexible retaining element biased radially inwardly or outwardly may be provided on the lock element and/or on the dose setting element or dose setting mechanism, which co-operates with another retaining element or a cut-out or a recess or groove on the respective co-operating element, for example the dose setting element or dose setting mechanism or lock element, to establish a releasable coupling between the lock element and the dose setting element or dose setting mechanism. In some preferred embodiments, this coupling is then released when an ampoule is or has been introduced into the injection device to a pre-defined length, e.g. by a sliding movement of at least one retaining element caused by the ampoule being introduced and guided by a guide profile.

In some embodiments, the present invention relates to an injection device with a dose setting mechanism of the type described above and an ampoule insertion part such as an ampoule sleeve or, alternatively, an ampoule body, able to co-operate with the lock element, the dose setting element or dose setting mechanism as it is inserted. This is accomplished, for example, by moving into contact with the lock element or dose setting mechanism and causes the dose setting mechanism or dose setting element to be released during the movement or sliding action of the dose setting mechanism or lock element relative to the injection device or to a housing of the injection device caused by the movement of the ampoule as it is being inserted. In this respect, the lock element may also be part of the dose setting mechanism.

In some preferred embodiments, the injection device has a guide element, such as a ramp or a profile, extending at an angle with respect to the axial direction. The guide element is disposed relative to a retaining element of the lock element or dose setting mechanism so that an axial sliding movement of the lock element or dose setting mechanism relative to the injection device causes at least one retaining element to be moved by the guide, such that the engagement between the lock element and the dose setting element or dose setting mechanism is released.

In some preferred embodiments, a flange is provided on the injection device. The flange pushes against a stopper of the ampoule, e.g. a two-chamber ampoule, when it is introduced or screwed in. This causes the stopper to be pushed into the ampoule as the ampoule is being screwed into the injection device so that the substances contained in the two-chamber ampoule are mixed.

Another embodiment of the present invention relates to a method of preparing an injection device for dispensing a substance from a two-chamber ampoule, wherein the two-chamber ampoule is introduced into the injection device, e.g. screwed in, and a lock of a setting element or priming element of the injection device is released when the ampoule has been introduced far enough into the injection device that the substances contained in the two-chamber ampoule have been properly mixed. In some embodiments, the lock is an anti-rotation lock.

BRIEF DESCRIPTION OF THE DRAWINGS

FIG. 1 is a perspective view illustrating one embodiment of the present invention, a dose setting mechanism with a released lock element;

FIG. 2 is a side view of the dose setting mechanism illustrated in FIG. 1 prior to mixing;

FIG. 2A is a sectional view along line C-C in FIG. 1;

FIG. 2B is a detail D from FIG. 2A;

FIG. 3 shows the dose setting mechanism illustrated in FIG. 2 once the two-chamber ampoule has been fully screwed in and mixed;

FIG. 3A is a sectional view along line A-A in FIG. 3;

FIG. 3B illustrates detail B from FIG. 3A;

FIG. 4 is a plan view of an embodiment of an injection device in accordance with the present invention with the mechanism locked;

FIG. 4A is a sectional view along line A-A in FIG. 4;

FIG. 5 shows the injection device illustrated in FIG. 4 with the mechanism released; and FIG. 5A is a sectional view along line B-B in FIG. 5.

DETAILED DESCRIPTION

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making the invention and/or its components may be selected from appropriate materials such as metal, metallic alloys, ceramics, plastics, etc.

FIG. 1 is a perspective view illustrating one embodiment of a dose setting mechanism in accordance with the present invention which can be inserted in an injection device. A lock sleeve disposed at least in the front or distal part inside the housing of the injection device when the dose setting mechanism is inserted has an orifice 8a in which a retaining element 1a of the locking ring 1, which is biased radially inwardly and serves as the lock element, locates once the ampoule 5 has been screwed in.

In the initial position illustrated in FIG. 2, the locking ring 1 is mounted so that it can not rotate relative to the injection device or the housing of the injection device by an orifice in the housing, in which an element of the locking ring 1 such as a retaining element 1a is received. Thus, the dose setting sleeve 2 is mounted in the injection device so that it can not rotate due to the retaining element 1a locating in the orifice or groove 2a of the dose setting sleeve 2. The locking ring 1 is biased in the distal (or forward) direction of the injection device by a spring force, for example.

FIG. 2 is a side view showing the dose setting mechanism illustrated in FIG. 1, with the retaining element 1a of the locking ring 1 lying relative to the groove 8a of the sleeve 8 so that there is still a distance d to the proximal end of the groove 8a shown on the right-hand side of FIG. 2.

FIG. 2A is a view in section along line C-C indicated in FIG. 2, showing how the retaining element 1a, biased radially inwardly, is received in a groove 2a of the dose setting sleeve 2 and thus blocks any rotating movement of the dose setting sleeve 2 relative to the housing 3 of the injection device. When an ampoule 5 inserted in an ampoule sleeve 4 is screwed into the injection device to push the rear or proximal stopper 5a of the ampoule into the two-chamber ampoule 5 by the flange 6 mounted on the threaded rod 7 of the injection device to enable mixing in the two-chamber ampoule 5. The proximal end of the ampoule sleeve 4 illustrated on the right-hand side of FIG. 2A moves into contact with the front face 1b of the locking ring 1 when the ampoule sleeve 4 with the ampoule 5 in it has been screwed far enough into the injection device for the flange 6 to have been pushed sufficiently far into the ampoule 5 to have caused complete or almost complete mixing of the two-chamber ampoule. When the ampoule sleeve 4 is screwed farther into the injection device, the locking ring 1 is pushed to the right in FIG. 2A, in other words in the proximal direction, due to the contact of the proximal end of the ampoule sleeve 4 with the contact face 1b. This causes the guide profile 1c provided in the locking ring 1 to move into contact with the ramp 3a which is not able to slide relative to the injection device. The sliding movement of the locking ring 1 causes the retaining element 1a to be pushed outwardly against the inwardly directed biasing force of the retaining element 1a, as illustrated in detail B of FIG. 3B, thereby releasing the retaining element 1a from its position located in the groove 2a of the dose setting sleeve 2 so that the dose setting sleeve 2 is no longer prevented from rotating relative to the injection device.

FIGS. 3 and 3A illustrate the status of the dose setting mechanism after the locking ring 1 has moved slightly in the proximal direction by the distance d to unlock the dose setting sleeve 2.

After the ampoule 5 has been fully mixed and the anti-rotation lock 1a, 2a of the dose setting sleeve 2 has been released, the dose setting sleeve 2 can be rotated by a user to set a dose or prime the injection device, so that a dose is dispensed from the ampoule 5 during an injection.

The setting mechanism is therefore mechanically locked by the two fork-shaped lock pawls 1a of the locking ring, which extend through co-operating recesses 2a of the rotating or dose setting sleeve 2. Since the pen is primed by rotating the rotating ring 2, this is now not possible because the rotation is prevented by the locking ring 1.

To unlock the mechanism, the ampoule sleeve 4, which was screwed into the dose setting or setting mechanism to mix the two-chamber ampoule 5, is screwed in. On the last approximately 2 mm of the screwing-in movement, the locking ring 1 is moved from the locked position into the unlocked position by the ampoule sleeve 4. To this end, the locking ring 1 has inclined surfaces on the inner faces of the two fork-shaped lock pawls 1a which complement the inclined surfaces 3a of the guide sleeve or housing. As a result, the two lock pawls 1a are pushed out and thus release the dose setting sleeve 2 or mechanism.

The retaining element 1a or locking ring 1 is designed so that it is pushed in the proximal direction by the ampoule sleeve 4, which is screwed into the pen when the ampoule 5 is screwed in to mix the substance. A ramp or slide surface 3a, provided on the housing of the injection device, causes the retaining element 1a of the locking ring 1, which is moved relative to the ramp 3a by the ampoule sleeve 4, to be pushed radially outwardly and thus release the anti-rotation lock of the dose setting sleeve 2. Consequently, once the ampoule sleeve 4 has been fully pushed in, a dose can be set by rotating the dose setting sleeve 2. This ensures that the dose setting sleeve 2 can not be rotated until the ampoule sleeve 4 has been fully screwed into the pen, in other words far enough for the ampoule sleeve 4 to hit the locking ring 1 and push it by a farther distance into the injection device.

FIG. 4 is a plan view showing an injection device with the mechanism locked, as illustrated along section A-A indicated in FIG. 4A. As may be seen from FIG. 4A, the retaining element 1a, which need not necessarily be mounted on a locking ring, is urged radially inwardly and locates or lodges in a groove 2a of the dose setting sleeve 2, thus blocking or locking any rotating movement of the dose setting sleeve 2 relative to the housing 3 of the injection device. The ampoule 5 inserted in the ampoule sleeve 4 can be screwed into the injection device, as illustrated in FIGS. 5 and 5A. As a result, the guide profile 1c moves into contact with the ramp 3a, which is not able to move relative to the injection device and is pushed outwardly against the biasing action of the retaining element 1a due to the movement of the retaining element 1a, once the proximal end of the ampoule sleeve 4 has reached the contact surface 1b as may be seen from FIG. 5A. As a result, the engagement of the retaining element 1a in the groove 2a of the dose setting sleeve 2 is released so that the dose setting sleeve 2 is no longer prevented from rotating relative to the injection device. In the case of the injection device illustrated in FIG. 5A, the ampoule has therefore been completely or almost completely inserted and a dose setting or setting movement can take place because the dose setting sleeve 2 has been released by outward movement of the retaining element 1a.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A lock element for a dose setting mechanism of an injection device, the lock element comprising at least one retaining element flexibly joined to the lock element and a contact surface, wherein the at least one retaining element is co-operable with a groove of a dose setting element of the dose setting mechanism, whereby a rotational dose setting movement of the dose setting element is prevented when the lock element is in an initial position in which the at least one retaining element is arranged in the groove, and wherein the contact surface contacts an ampoule insertion part upon insertion of the ampoule insertion part into the injection device and moves the lock element axially relative to the injection device in an ampoule insertion direction into an unlocked position in which the at least one retaining element flexes radially out of the groove and the dose setting element rotates in the rotational dose setting movement.

2. The lock element as claimed in claim 1, wherein the lock element is annular.

3. The lock element as claimed in claim 1, wherein the at least one retaining element is biased radially.

4. The lock element as claimed in claim 3, wherein the at least one retaining element is arranged transversely to the contact surface.

5. The lock element as claimed in claim 1, comprising at least two retaining elements.

6. The lock element as claimed in claim 1, wherein the ampoule insertion part comprises an ampoule sleeve.

7. The lock element as claimed in claim 1, wherein the ampoule insertion part comprises an ampoule body.

8. A dose setting mechanism for an injection device comprising a lock element, the lock element comprising at least one retaining element flexibly joined to the lock element, the at least one retaining element defining a guide profile, wherein the at least one retaining element is co-operable with a groove of a dose setting element of the dose setting mechanism, whereby a setting movement of the dose setting element is prevented when the lock element is in an initial position in which the at least one retaining element is arranged in the groove, and wherein the guide profile guides an axial movement of the lock element relative to the dose setting element as the lock element moves into an unlocked position in which the guide profile causes the at least one retaining element to pivot radially out of the groove such that the dose setting element engages in the setting movement.

9. An injection device comprising a dose setting mechanism comprising a lock element, the lock element comprising at least one retaining element flexibly joined to the lock element, the retaining element co-operable with a groove of a dose setting element of the dose setting mechanism, wherein a setting movement of the dose setting element is prevented when the lock element is in an initial position in which the at least one retaining element is arranged in the groove, wherein the injection device further comprises a two-chamber ampoule arranged in an ampoule sleeve, wherein said ampoule sleeve or said two-chamber ampoule is co-operable with the lock element so that the lock element is moved from the initial position into an unlocked position after a pre-defined insertion movement of the ampoule sleeve or the two-chamber ampoule so that the at least one retaining element is radially flexed and moved out of the groove and the dose setting element engages in the setting movement, and wherein the injection device is configured such that lock element remains in the initial position until contents of the two-chambers of the two-chamber ampoule are substantially mixed.

10. The injection device as claimed in claim 9, further comprising a flange moveable into contact with a stopper of the two-chamber ampoule to enable mixing as the two-chamber ampoule is being introduced into the injection device prior to the pre-defined insertion movement.

11. The injection device as claimed in claim 10, further comprising a guide profile on the injection device, with which a lock element guide profile is able to move into contact to release the lock element from the initial position due to a movement of the lock element relative to the guide profile.

12. The injection device as claimed in claim 11, wherein the lock element is mounted in the injection device so that it is prevented from rotating.

13. The injection device as claimed in claim 12, wherein the lock element is biased in the direction opposite an ampoule insertion direction.

14. The injection device as claimed in claim 11, wherein the lock element guide profile is positioned on a proximal end of the lock element.

15. The injection device as claimed in claim 11, wherein the lock element guide profile is positioned spaced-apart from the proximal and distal ends of the lock element.

16. A method of preparing an injection device for dispensing a substance from an ampoule, the method comprising the steps of:
 establishing a lock between a dose setting element and a lock element, said lock formed between at least one retaining element flexibly joined to the lock element and a groove of the dose setting element and preventing a rotational dose setting movement of the dose setting element,
 introducing the ampoule into the injection device, and
 releasing the lock, said releasing occurring when the ampoule has been introduced far enough into the injection device for the substance in the ampoule to be dispensed and for the lock element to be moved axially within the injection device causing at least one retaining element to radially flex and pivot out of the groove of the dose setting element, and
 rotating the dose setting element in the rotational dose setting movement.

17. A method of preparing an injection device for dispensing a substance from a two-chamber ampoule, the method comprising the steps of:
 establishing a lock between a dose setting element and a lock element, said lock formed between at least one retaining element flexibly joined to the lock element and a groove of the dose setting element and preventing a rotational dose setting movement of the dose setting element;
 introducing the two-chamber ampoule into the injection device,
 releasing the lock, said releasing occurring by an axial movement of the lock element within the injection device when the two-chamber ampoule has been introduced far enough into the injection device for substances in the two chambers to be appropriately mixed and the at least one retaining element has radially flexed and pivoted out of the groove of the dose setting element, and
 rotating the dose setting element in the rotational dose setting movement.

* * * * *